United States Patent [19]

Mims

[11] 4,254,770

[45] Mar. 10, 1981

[54] APPARATUS AND METHOD FOR ALLEVIATING PHYSIOLOGICAL CONDITIONS BY DIRECTED SPRAY OF LIQUID TOWARD BODY TISSUE

[75] Inventor: Matlock M. Mims, Beverly Hills, Calif.

[73] Assignees: Gregory Bergeron, Reno, Nev.; Robert J. Heiner, Playa Del Rey, Calif.

[21] Appl. No.: 79,312

[22] Filed: Sep. 27, 1979

Related U.S. Application Data

[63] Continuation of Ser. No. 885,124, Mar. 10, 1978, Pat. No. 4,203,437.

[51] Int. Cl.3 .......... A61M 3/00

[52] U.S. Cl. .......... 128/229; 128/248

[58] Field of Search .......... 128/248, 229, 226, 227, 128/224, 232, 83

[56] References Cited

U.S. PATENT DOCUMENTS

| | | | |
|---|---|---|---|
| 587,767 | 8/1897 | Stoll | 128/226 |
| 761,217 | 5/1904 | Gilbert | 128/226 |
| 1,779,753 | 10/1930 | Schlumbohm | 128/226 |
| 3,308,491 | 3/1967 | Spence | 128/83 UX |
| 3,416,529 | 12/1968 | Weisman | 128/232 |
| 3,675,659 | 7/1972 | Wideman | 128/395 |
| 3,769,977 | 11/1973 | Victory | 128/229 |
| 3,773,046 | 11/1973 | Rosenberg | 128/230 |

*Primary Examiner*—John D. Yasko

*Attorney, Agent, or Firm*—Romney, Schaap, Golant, Disner & Ashen

[57] ABSTRACT

The present invention provides a therapeutic spray apparatus and method for alleviating human ailments and conditions thereof. The apparatus comprises a pad capable of being disposed in an area, such as a bathtub, for a person to reside in a sitting position and which pad is capable of supporting the buttocks and a portion of the thighs of the individual sitting thereupon. The pad also serves as a housing to contain certain of the components forming part of the apparatus in a kit form. One of the components of the apparatus is a nozzle capable of being disposed within an aperture in the pad and has a nozzle opening capable of directing water toward the groin area of an individual sitting upon the pad. A hose is connected to the nozzle on its underside and is capable of being connected to a source of water under pressure, such as tap water, such that the tap water is directed as a spray, and preferably as an intermittent spray, toward the groin area. In this way, it is possible to alleviate conditions of prostate gland ailments, vaginitis, hemorrhoids, anal and anal canal disorders and like problems. The hose and the nozzle can be easily disposed within a recessed means formed within the pad. Moreover, a supporting element, in the form of a retaining plate, disposed in the pad may be secured to a wall or similar surface for holding the pad in an upright position when not in use. The retaining plate can also be used for other functional purposes, such as a soap dish or the like.

6 Claims, 16 Drawing Figures

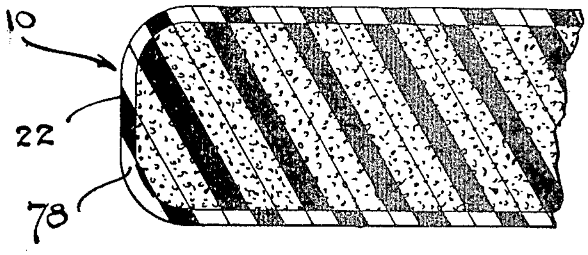
FIG. 13
FIG. 14
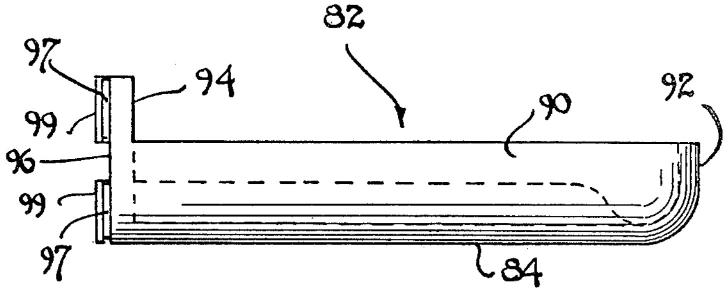
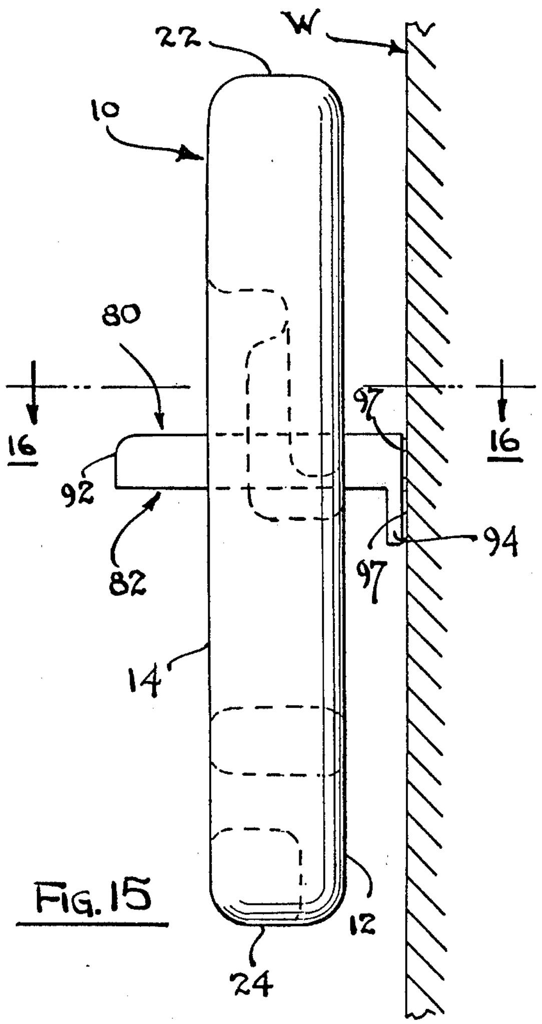
FIG. 15
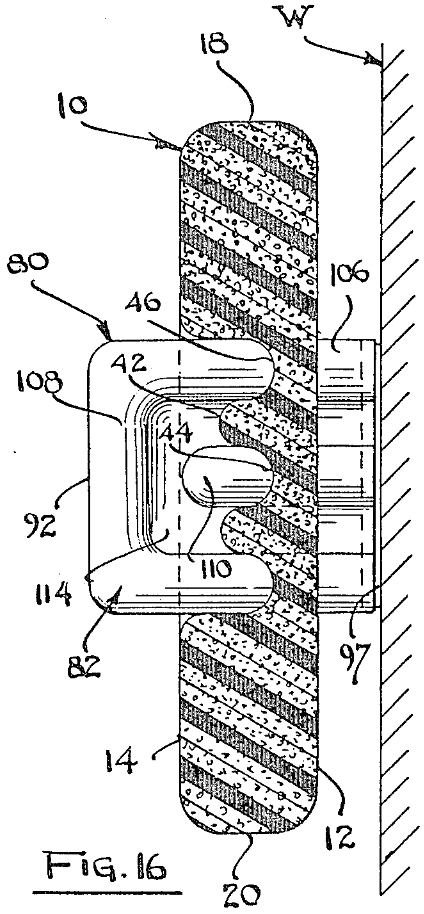
FIG. 16

APPARATUS AND METHOD FOR ALLEVIATING PHYSIOLOGICAL CONDITIONS BY DIRECTED SPRAY OF LIQUID TOWARD BODY TISSUE

RELATED APPLICATION

This application is a continuation of my copending application Ser. No. 885,124, filed Mar. 10, 1978, now U.S. Pat. No. 4,203,437 for Apparatus and Method for Alleviating Physiological Conditions by Directed Spray of Liquid Toward Body Tissue.

BACKGROUND OF THE INVENTION

1. Purpose of the Invention

This invention relates in general to certain new and useful improvements in apparatus and method for alleviating physiological conditions and, more particularly, to apparatus and method for alleviating such physiological conditions and ailments by directing a spray of liquid toward body tissue of an individual and which also provides a unique means of packaging the components of the apparatus in the form of a small compact kit.

2. Brief Description of the Prior Art

There have been many devices utilized to clean portions of the human body, as for example, in the crotch area, and which devices provide for a directed stream of water. For example, in U.S. Pat. No. 3,416,529 to Weisman, a base unit is provided for a person to sit in a position where the crotch of the person is disposed in relation to an opening. The base unit includes a container for holding a cleaning fluid which is transported to the crotch area by means of syringe. The syringe may be used for purposes of directing a stream of water into the vagina or the anus of the individual. In addition, the device may be transported by means of a handle.

There have also been other fluid treatment devices, as for example, taught in the McCarthy U.S. Pat. No. 3,288,140. This patent teaches of a fluid treatment device for use in conjunction with a conventional commode seat. The device employs an upwardly directed nozzle which is supplied with liquid from a bag forming part of the device through a flexible hose. The nozzle can be connected through a hose or tube to a water source for introducing water to and through the nozzle of the device. In like manner, U.S. Pat. No. 3,675,659 to Wideman discloses a device upon which a patient may sit for treatment in the groin area with heated air. There are other patents which relate to bidet devices and douche devices, as for example, in U.S. Pat. No. 1,779,753 to Schlumbohm and U.S. Pat. No. 3,773,046 to Rosenberg.

Briefly, the present invention relates to the use of a device and a method for projecting a spray of water such as tap water toward the tissue external to the prostate gland of men to relieve prostate gland conditions or toward the vaginal region of a woman in order to alleviate vaginitis and similar conditions. The present invention also can be used to project water to the anus and anal track to alleviate hemmorhoids or similar problems or to other external tissue on the body. In addition, the invention can be packaged in a single unit in which a portion of the packaged unit provides a pad for the user to sit on when the device is being used.

OBJECTS OF THE INVENTION

It is, therefore, the primary object of the present invention to provide an apparatus for directing a stream of water toward body tissue of an individual and which apparatus comprises a pad for a person to sit upon and also serves as the housing for storage of the components forming part of the apparatus.

It is another object of the present invention to provide an apparatus of the type stated which is uniquely designed for directing a spray of water, such as tap water, to the groin area of an individual sitting upon the pad in order to treat prostate gland problems, vaginitis, hemorrhoids and other anal disorders and like conditions.

It is a further object of the present invention to provide an apparatus of the type stated which includes several components and which components can be stored in a recess formed in part of the pad and in which one or more of the components serve other functions apart from the apparatus.

It is an additional object of the present invention to provide an apparatus of the type stated which can be made at a relatively low cost but which is nevertheless highly reliable in its operation and durable in its construction.

It is another salient object of the present invention to provide a method for projecting a stream of liquid toward body tissue in order to alleviate various physiological ailments and conditions thereof, and which also provides for packaging of the components in a single container and where the container serves as a pad for use in treatment.

It is also an object of the present invention to provide a method of the type stated in which water from a tap source can be directed toward the groin area of an individual in order to treat prostate gland problems, vaginitis, hemmorrhoids and other anal disorders and like conditions.

With the above and other objects in view, my invention resides in the novel features of form, construction, arrangement and combination of parts presently described and pointed out in the claims.

BRIEF DESCRIPTION OF THE DRAWINGS

Figure 2:
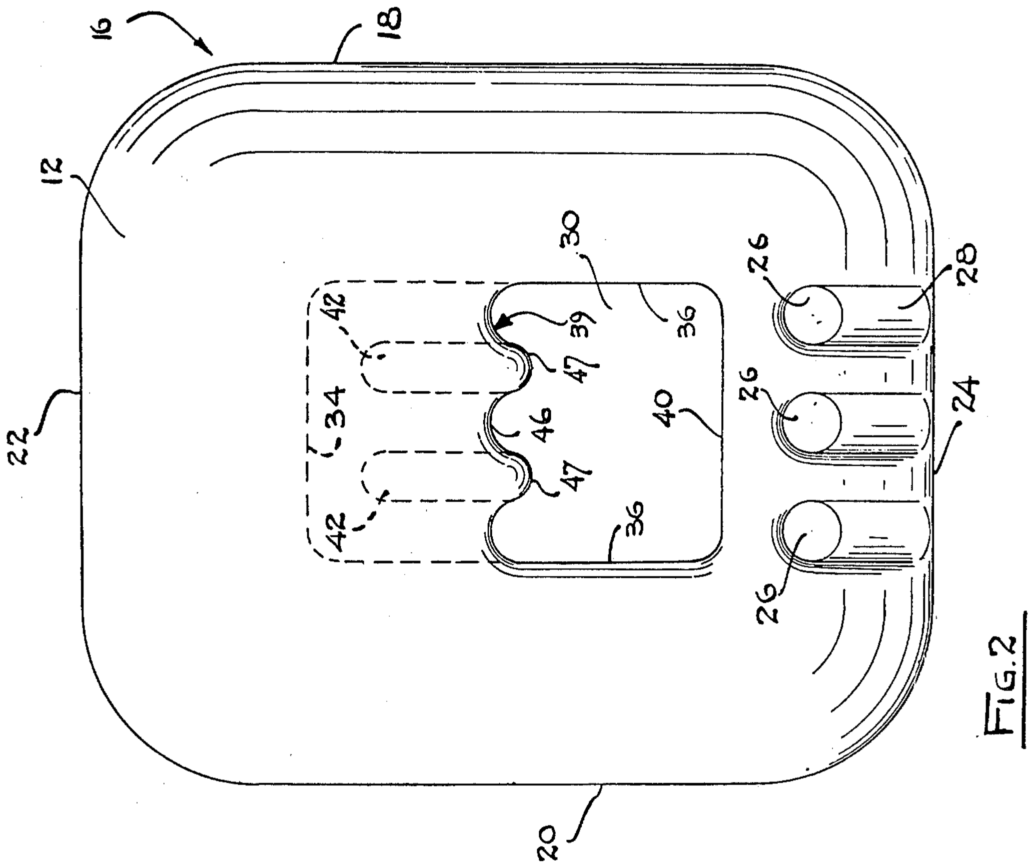
Figure 1:
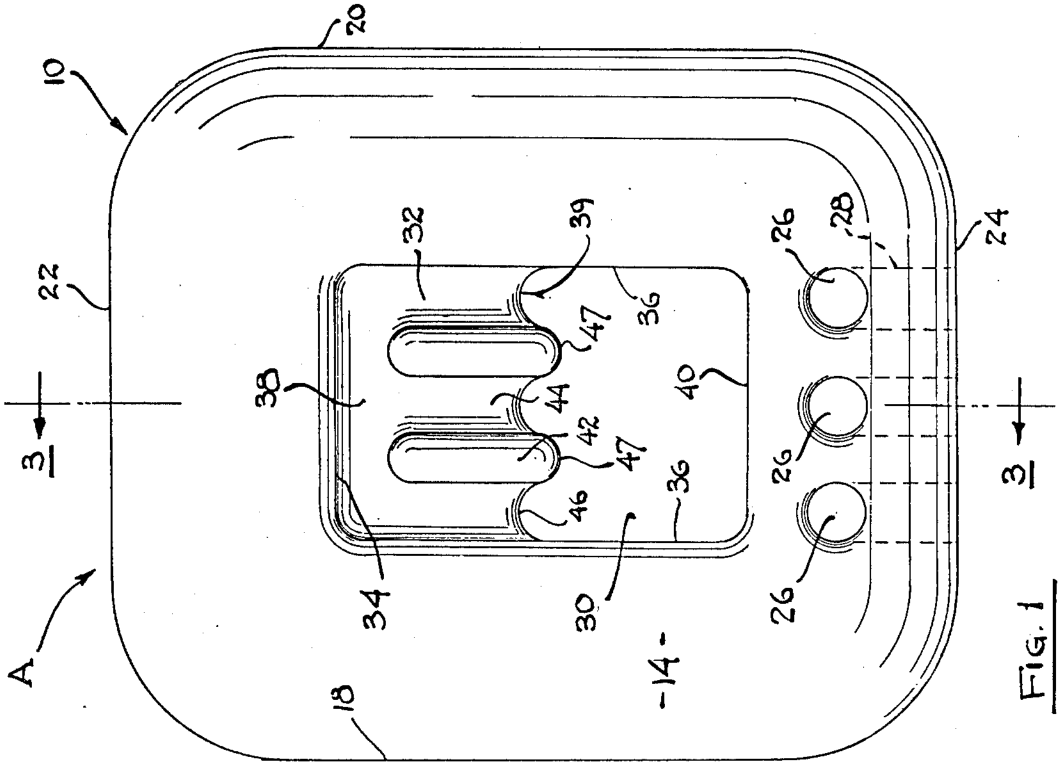
Figure 3:
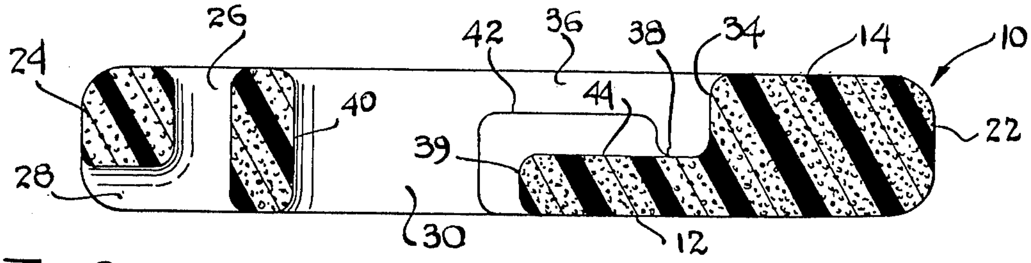
Figure 4:
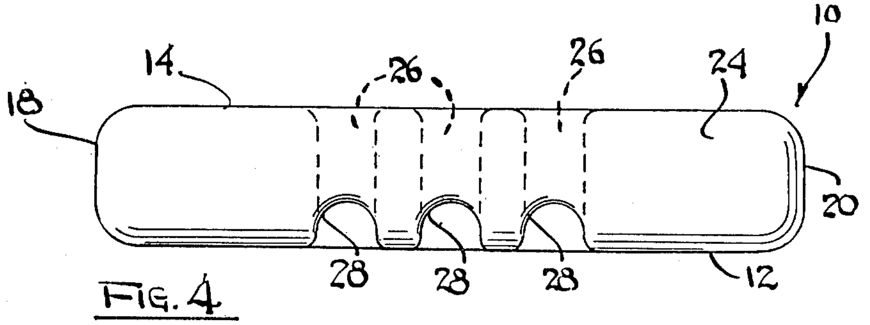
Figure 7:
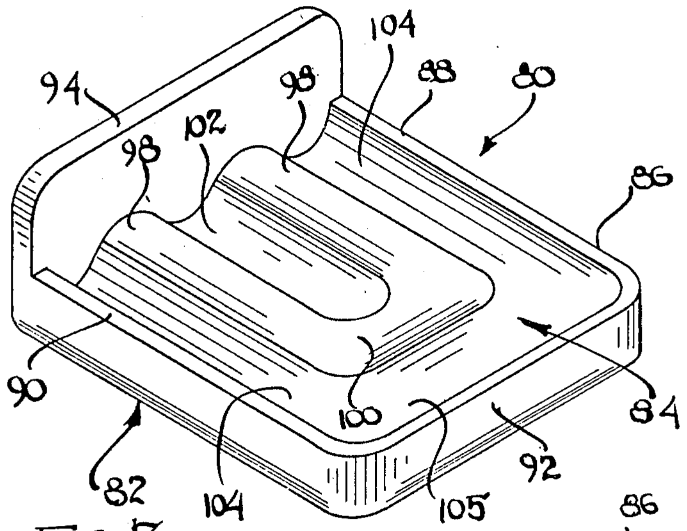
Figure 8:
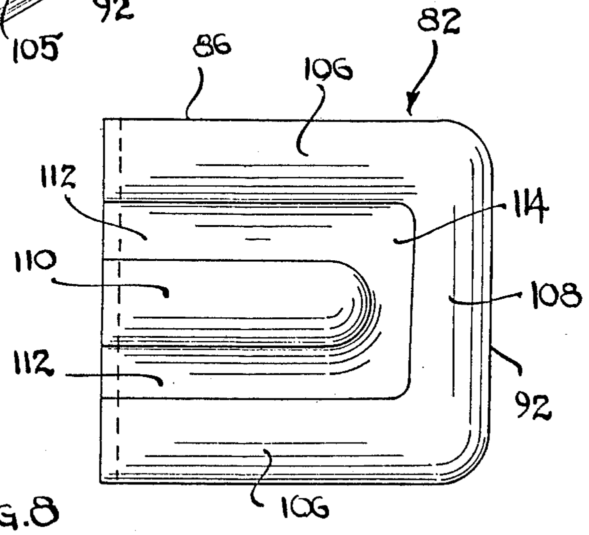
Figure 6:
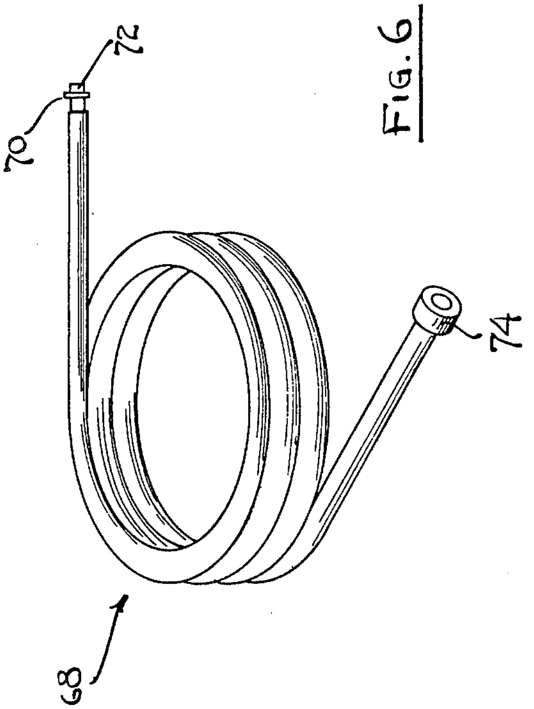
Figure 9:
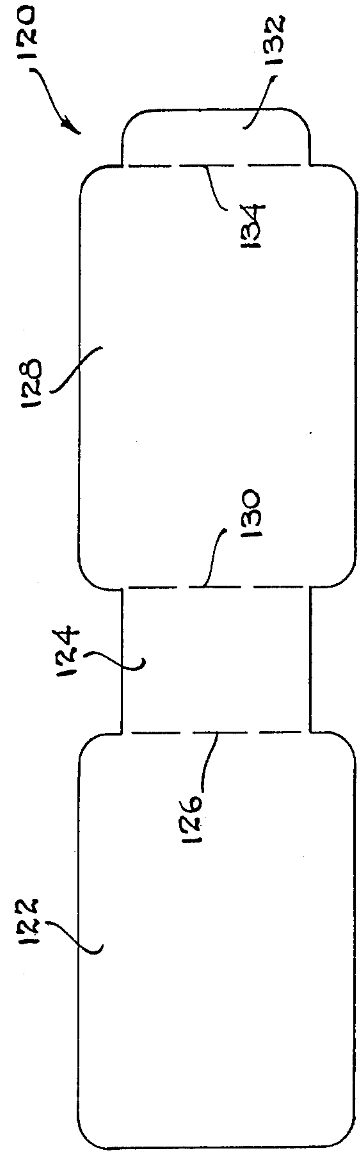
Figure 5:
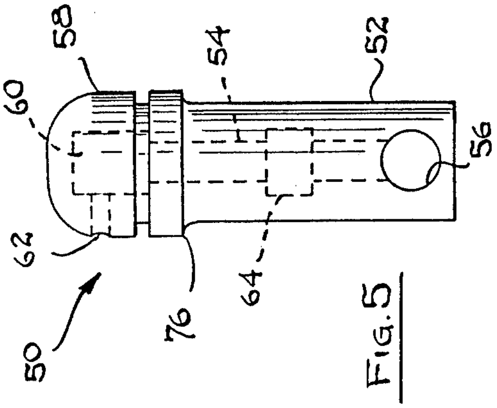
Figure 10:
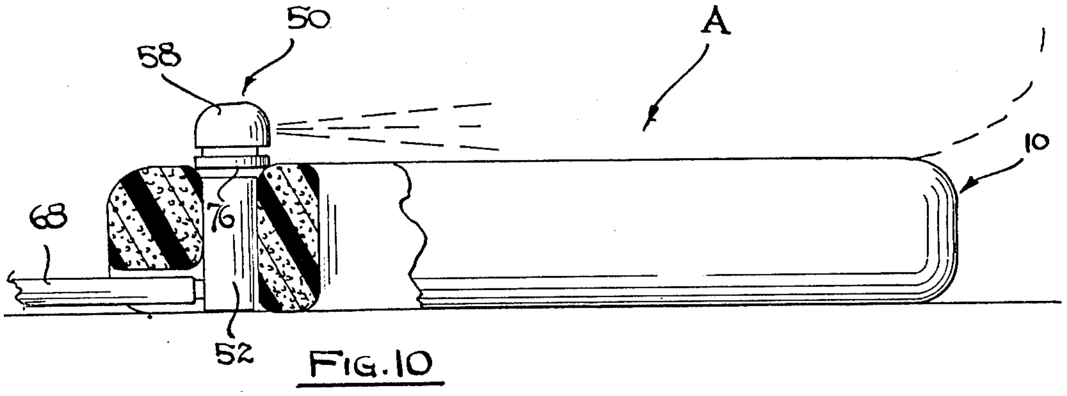

Having thus described the invention in general terms, reference will now be made to the accompanying drawings in which:

FIG. 1 is a top plan view of a pad forming part of the therapeutic spray apparatus of the present invention;

FIG. 2 is a bottom plan view of the pad of FIG. 1;

FIG. 3 is a vertical sectional view taken along line 3—3 of FIG. 1;

FIG. 4 is an end elevational view of the pad of FIG. 1;

FIG. 5 is a side elevational view of a nozzle used in connection with the apparatus of the present invention;

FIG. 6 is a perspective view of a hose forming part of the apparatus of the present invention;

FIG. 7 is a perspective view of a supporting element used in connection with the pad of FIGS. 1 and 2 for supporting the pad when not in use and retaining auxiliary components therein when in a physiological condition;

FIG. 8 is a bottom plan view of the supporting element of FIG. 7;

FIG. 9 is a top plan view of a retaining card forming part of the apparatus of the present invention;

FIG. 10 is a side elevational view, partially in phantom lines, and showing the nozzle in the operative position in the pad when the apparatus of the present invention is used.

Figure 11:
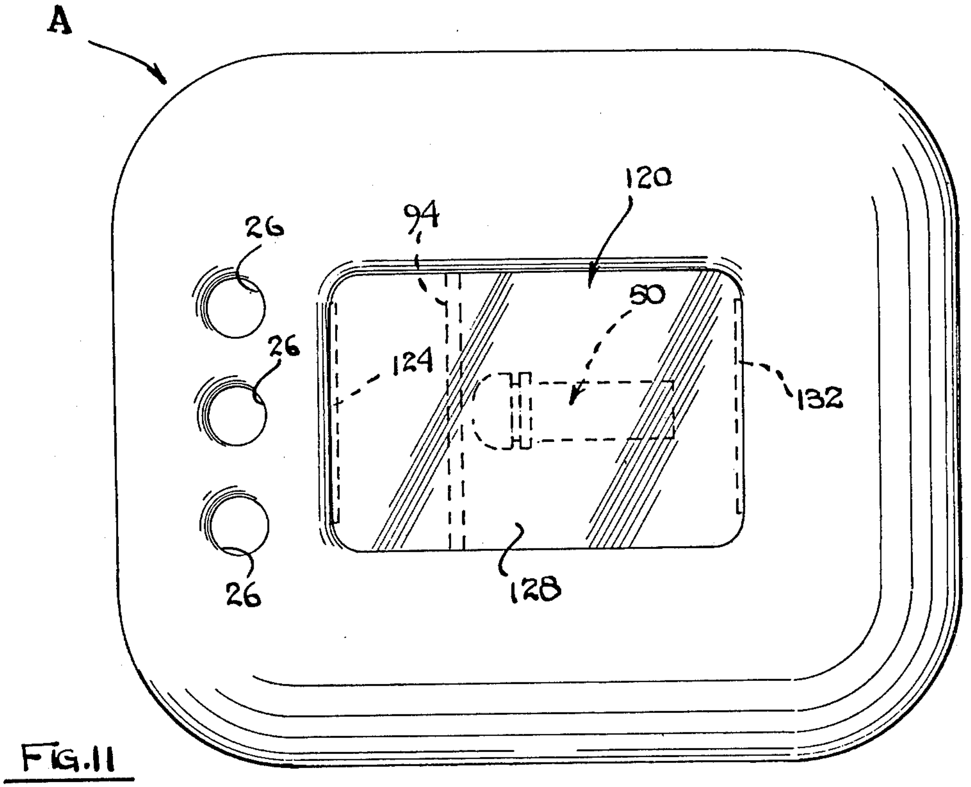
Figure 12:
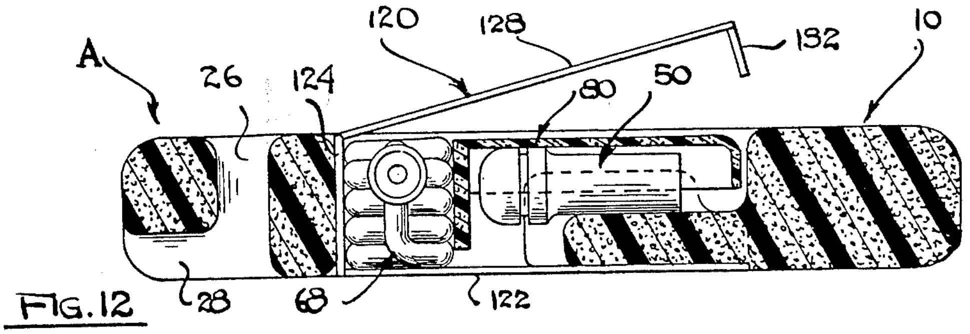

FIG. 11 is a top plan view, partially shown in phantom lines, and showing the nozzle and the supporting element in the pad when in the packaged position;

FIG. 12 is a vertical sectional view, somewhat similar to FIG. 3, and showing the components of the apparatus of the present invention in their packaged position;

FIG. 13 is a fragmentary vertical sectional view of a portion of the pad of FIGS. 1-3, and showing the pad with a substantially water impervious skin formed thereon;

FIG. 14 is a side elevational view of the supporting element forming part of the therapeutic spray apparatus of the present invention;

FIG. 15 is a side elevational view, partially shown in phantom lines, of the pad of FIG. 1 retained by the supporting element of FIG. 7 when the latter is secured to a supporting surface; and FIG. 16 is a horizontal sectional view of the pad retained by the supporting element as shown in FIG. 15 and taken along line 16—16 of FIG. 15.

DETAILED DESCRIPTION OF A PREFERRED EMBODIMENT

Referring now in more detail and by reference characters to the drawings which illustrate a preferred embodiment of the present invention, A designates a therapeutic spray apparatus comprising a pad 10 which is formed of a suitable plastic material such as styrofoam, polyethylene or the like. Styrofoam is one of the preferred materials due to the light-weight nature thereof and also due to the rigidity. Other forms of plastic materials which are highly effective are various polyurethanes.

The pad 10 is generally comprised of a bottom wall 12 and a top wall 14 which are connected together by a peripherally extending side wall portion 16 comprised of longitudinally extending side walls 18 and 20 connected by transverse side walls 22 and 24. As indicated previously, the top and bottom walls 14 and 12 along with the side wall portion 16 surround a solid interior core, except for removed portions, as hereinafter described. The top wall 14 is generally parallel with the bottom wall 12 as illustrated in FIGS. 1 and 2 of the drawings.

A plurality of vertically disposed apertures 26 (three as shown) extend from the top wall 14 to the bottom wall 12, in the manner as illustrated in FIGS. 1, 2 and 3 of the drawings. The apertures 26 are generally cylindrically shaped and are sized and located to provide receiving apertures for the fingers of an individual in order to carry the pad 10 and also to receive portions of the apparatus as hereinbefore described in more detail. By further reference to FIGS. 1-3, it can be observed that three longitudinally extending slots 28 are formed within the bottom wall 12 and intersect each of the apertures 26, respectively, in the manner as illustrated. Thus, in order to carry the pad, the user will insert three fingers of the hand wihin the three apertures 26 and which may also rest within the elongate recesses 28. Thus, the recesses 28, along with the apertures 26, form a means for an individual to carry the pad 10 in a vertically disposed position for easy portability thereof.

The housing 10 is also provided with an enlarged opening 30 which extends between the top wall 14 and the bottom wall 12. Moreover, the top wall 14 is provided with a recessed area 32 somewhat rectangular in shape which is defined by an interior transverse side wall section 34 and interior longitudinal side wall sections 36 forming a shelf 38 which extends partially into the enlarged opening 30. The shelf 38 has a forwardly presented transverse end wall 39 at the enlarged opening 30 and is spaced from an interior transverse end wall section 40.

It can be observed that the shelf 38 is recessed beneath the top wall 14 and is provided with a plurality of upstanding ridges 42 which are semi-circular in cross section. Only two such ridges are shown, although it should be understood that any number of ridges could be employed. These ridges 42 separate a plurality of elongate spaced apart longitudinally extending recesses 44 (three as shown) therebetween. The recesses are semi-circular in shape and are concave with respect to the top wall 14. Moreover, grooves 46 are formed in the transverse end wall 39 adjacent each of the recesses 44, thereby forming a pair of spaced apart projections 47 in the manner as illustrated in FIG. 1 of the drawings. These grooves 46 face the transverse interior wall section 34 in the manner as illustrated.

Also provided with the apparatus A of the present invention is a spray nozzle 50 more fully illustrated in FIG. 5 of the drawings. The spray nozzle 50 comprises an elongate shank 52 having a hollow interior defining an elongate liquid receiving duct 54 which communicates at its lower end with an inlet aperture 56 extending radially into the shank 52. The shank 52 may be integral with an enlarged head 58 having an interior chamber 60 and the latter of which communicates with the duct 54. In addition, the chamber communicates with one or more spray emitting apertures 62 on the head 58 which is capable of directing a spray of liquid toward the body tissue of an individual.

In a preferred embodiment of the invention, the enlarged head 58 is adjustably mounted on the shank 52 so that the spray emitting apertures may be adjustably positioned. In this way, a spray of liquid may be directed in a generally horizontal path or shifted so that the liquid is directed at an angle with respect to the horizontal. The means for adjustably mounting the enlarged head 58 on the shank 52 is conventional in construction and is therefore neither illustrated nor described in any further detail herein.

A valve 64 may be located within the shank 52. In this case, the valve 64 is a conventional type which is designed to provide a spray of liquid from the aperture 62 on an intermittent basis such that the spray of liquid occurs in a pulsating manner. However, it should be understood that the valve 64 could be eliminated in order to provide a constant jet stream of water. Nevertheless, in the preferred aspect of the present invention, the valve 64 is highly desirable in order to provide the pulsating stream of liquid. Moreover, the pulsating stream of liquid is preferably luke-warm water provided from a conventional water tap.

As indicated previously, the valve 64 is of a conventional construction and is designed to permit water passage only on an intermittent basis. Thus, the valve 64 is of the type which will receive a stream of water under pressure and will only open when the pressure has exceeded a predetermined threshold level. Thereafter, the valve 64 will close until the pressure is again increased to the threshold level whereupon the valve 64 will open. In this way, a constant intermittent stream is provided through the chamber 60 and through the outlet aperture 62.

A water hose 68, as illustrated in FIG. 6, is also provided in the apparatus A of the present invention. In this case, the water hose 68 is provided at one end with a fitting 70 having a relatively rigid tube section 72 which is capable of extending within the aperture 56. While the hose may be formed of a flexible material, such as a rubber material, the fitting 70 including the tube section 72 is formed of a fairly rigid plastic material. At the other end, the hose 68 is provided with a fitting 74 which may be the conventional type for fitting on a water outlet tap. Thus, the fitting 74 may be cylindrical in nature and provided with internal or external threads for screw-type attachment. In like manner, the fitting 74 may be somewhat of a flexible material for fitting over or into the outlet tap on a bathtub or a sink. In each case, the fittings 70 and 74 would be provided with the conventional seals as may be necessary in order to prevent water leakage.

The pad 10 along with the nozzle 50 and the hose 68 constitute the principal operating components of the apparatus A. In this case, it can be observed that the shank 52 is provided with an overall outer diameter to fit within one of the apertures 26 and which extends from the top wall 14 toward the bottom wall 12, as illustrated in FIG. 10 of the drawings. In this respect, it can be observed that the enlarged head 58 is provided with a shoulder 76 which engages the top wall 14 while the remainder of the shank 52 extends through the aperture 26 toward the bottom wall 12. Inasmuch as the apertures 26 are intersected by the recesses 28, the lower end of the shank 52 extends beyond the apertures 26. Nevertheless, the size of the shank 52 between the enlarged head 58 and the bottom portion thereof is such that it will not extend beyond the bottom wall 12.

The fitting 70 on the hose 68 is capable of being connected to the lower end of the shank 52 such that it extends over the water inlet aperture 56, or otherwise is provided with the tube 72 to extend within the water inlet aperture 56. In this way, the fitting 74 may be connected to a conventional water outlet such as a conventional water tap providing water to the fitting 70 and hence the nozzle 50. The water will enter through the hose 68, through the end into the aperture 56 into the chamber 60. As water accumulates in the chamber 60, it will be directed outwardly through the spray aperture 62. If the valve 64 is provided, the water will be controlled so that it is provided on an intermittent basis.

The hose 68 is preferably formed of a flexible and foldable rubber material, although a plastic material such as polyethylene could be employed. Again, the nozzle 50 and the fitting 74 are also conventional in their construction and may be formed of a more rigid plastic material or otherwise any other forms of materials as may be desired. The nozzle 50 is similarly preferably formed of a fairly rigid plastic material, such as a polyethylene, polybutadiene, polypropylene, polystyrene or the like. The valve 64 within the nozzle 50 may be similarly formed of a plastic material, although the valve 64 may also be formed of metallic materials in a conventional manner.

The user of the apparatus A will generally dispose the pad 10 within an area which is capable of collecting waste water, as for example, a bathtub. In this case, the bottom wall 12 will be seated against the upwardly presented bottom surface of the bathtub with the upper wall 14 presented upwardly for the user of the apparatus to sit upon. In this case, it can be observed that the user of the apparatus A can rest upon the upper surface near the rear portion thereof, that is with his buttocks supported on the upper surface 14 adjacent the end wall 22, and have his thighs and perhaps portions of the bottocks supported by the upper surface 14 along the longitudinal side margins 18 and 20.

The shank 52 of the nozzle 50 is then inserted within one of the apertures 26, preferably the centermost of the apertures, with the spray emitting opening 62 directed toward the groin area of the individual sitting on the pad 10. In the case of the male, the spray of water would be directed toward the area immediately under the testicles in order to alleviate prostate gland problems. In the case of the female, the spray would be directed toward the vaginal opening in order to alleviate conditions of vaginitis and similar problems. It should also be observed that the individual could support his knees on the upper surface 14 along the elongate strips defined by the two longitudinal margins 18 and 20 and the inner longitudinal margin 36 with the anus of the individual located so that the spray from the nozzle 50 can be directed toward the anus of the individual.

The pad 10 is preferably formed of a somewhat soft or yieldable plastic material, such as a somewhat yieldable polyurethane or similar plastic, to provide some softness or resiliency when sat upon or otherwise when supporting the user with his knees on the pad 10. In this respect, a suitable and conventional foaming agent could be injected into the plastic material during the molding of the plastic pad 10. The other components of the apparatus of the present invention would not require this resiliency.

In addition, the pad could be molded in such manner that an outer essentially water impervious skin 78 is formed on the exterior of the pad, in the manner as illustrated in FIG. 13 of the drawings. It should be understood that this outer skin is generally integral with the remaining material forming the pad and is formed of the same material as the pad, but is created during the molding process. This water impervious skin 78 is desirable to prevent entrainment of water in the pad during periods of use which would otherwise increase drying time of the outer skin where not used. Moreover, this outer skin also eliminates or at least substantially reduces the problem of fungal or bacterial growth in the pad 10.

If desired, an outer skin 78 could be formed separately and adhered to the exterior surface of the pad, by adhesive means or otherwise, although this latter technique of forming a substantially water impervious skin is not as desirable as integrally forming the skin during the molding process due to cost and ease of manufacture. Also, if desired, a suitable known bactericide could be incorporated into the palstic material during the formation of the pad 10 to inhibit fungal and bacterial growth.

It has been found in connection with the present invention that it is possible to substantially alleviate many of the physiological conditions arising from ailments in the groin area, and particularly the discomfort arising from such ailments by directing a stream of water toward the groin area. The excess water will pass through the enlarged opening 30 and out of the drain of the bathtub or similar enclosure to receive the waste water.

The term "physiological conditions", as used herein, is used in the broad or generic sense to include pathological disorders as well. Moreover, the term "groin", as used herein, is used in the broad or generic sense to include not only the genital region, but the region surrounded by the buttocks of an individual including the anus and anal track, namely the entire region where the depressed part or fold of the abdomen joins the thighs of the legs of an individual.

The components of the apparatus can be packaged in a neat compact unit. In this case, the apparatus comprises an insert 80 in the form of a supporting element often referred to as a "retainer" or "retaining element". The supporting element is preferably formed of a fairly rigid plastic material, such as those plastic materials used in the formation of the nozzle 50. The insert 80 is more fully illustrated in FIGS. 7, 8 and 14 of the drawings. The insert 80 generally comprises a tray 82 having a bottom wall 84 with an upstanding peripheral side wall portion 86 having a pair of longitudinally extending side walls 88 and 90 and a transverse end wall 92. At its rearward end, the tray 82 is provided with a vertically disposed upstanding end plate 94, the latter of which has a vertical dimension greater than and extending upwardly above the peripheral side walls 88, 90 and 92. In this respect, the tray 82 and the end plate 94 could be formed of two units which are adhesively or otherwise secured together. Otherwise, and in the preferred aspect, the tray 82 and the transverse end plate 94 could be molded as an integral unit.

The bottom wall 84 is provided on its upper surface with a pair of longitudinally located upwardly extending projections 98 which are somewhat semicircular in cross section. These projections 98 are connected at their forwardmost end by means of a transversely extending projection 100 which is also semicircular in cross section and which is spaced inwardly from the vertically disposed side wall section 92, in the manner as illustrated in FIG. 7. It can be observed that the two upwardly extending projections 98 form a recess 102 therebetween and a pair of longitudinally extending recesses 104 adjacent the longitudinally extending side wall sections 88 and 90. The recesses 104 merge into a transverse recess 105 adjacent the end wall 92. It can be observed that the recesses 102, 104 and 105 and the projections 98 and 100 essentially define the bottom wall 84.

The tray 82 can be molded so that the undersurface of the bottom wall 84 of the tray 82 is an effective mirror image of the upper surface thereof. Thus, the undersurface of the bottom wall 84 is similarly provided with two longitudinally extending projections 106 and a transverse end wall projection 108 with an intermediate projection 110 extending toward, but not connected to, the transverse end wall projection 108. These projections on the undersurface of the bottom wall thereby form a pair of longitudinally extending recesses 112 therebetween which are connected by a transverse recess 114, as illustrated in FIG. 8.

The end plate 94 of the insert or retaining member 80 is provided on its rearwardly presented surface 96 with a pair of spaced apart double adhesive tapes 97, with each having a removable backing 99. In this way, the removable backing 99 can be pealed from the tapes 97 so that the tapes can be adhered to a wall or other supporting surface to thereby hold the supporting element in a generally horizontal position, that is with the tray 82 being disposed in a generally horizontal position. Generally, the supporting element 80 will be turned upside down so that the end plate 94 will be extending downwardly when secured to the wall or other supporting surface, for reasons which will presently more fully appear. It should be understood that other means for adhering the end plate 94 to a wall or supporting surface may be provided, as for example, drilled holes to receive mechanical fasteners, e.g. screws and the like.

The supporting element is uniquely designed to serve as a retainer for many of the components of the apparatus of the present invention when packaged. In addition, the supporting element 80 is designed so that it may be secured to a wall or similar supporting surface W in the manner as illustrated in FIGS. 15 and 16 to support the pad 10 when not in use. In this respect, it can be observed that the pad would be located in a vertically disposed position with the slots 28 and the projections 47 extending downwardly.

In order to support the pad 10 on the supporting element 80, the projections 47 will extend into the recesses 112 on the bottom side of the tray 82. Moreover, the projections 47 may be designed to fit into the recesses 112 in somewhat of a snap-fitting manner to retentively, but nevertheless removably, hold the pad 10 on the supporting element 80. In this way, the pad 10 may be hung on the supporting element 80 when not in use to drip dry. In addition, the hose 68 may be wrapped around the peripherally extending side wall portion 16 of the pad 10 and held against the corner area where the back transverse end wall 22 of the pad 10 engages the wall W or other supporting surface. For this purpose, the peripherally extending side wall portion 16 of the pad 10 may be provided with a groove (not shown) for receiving the hose 68 when wrapped around the pad 10.

The insert or supporting element 80 is also useful in retaining the hose 68 and the nozzle 50 within the opening 36 in the pad in a packaged condition, in a manner to be hereinafter described in more detail. However, it can also be observed that the insert 80 is also uniquely designed so that it is capable of performing other functions not necessarily associated with the use or packaging of the apparatus. For example, the insert 80 could be used as a soap dish. In this case, the upstanding plate 94 can be adjustably secured to a wall surface or other supporting structure in a generally upright position if desired. In addition, the bottom wall 84 could be provided with drainage apertures (not shown) as may often be employed in a conventional soap dish.

The supporting element or insert 80 along with the nozzle 50 and the hose 68 may all be retained within the opening 30 and on the shelf 38 by means of a foldable card 120, often referred to as a "cover member". The foldable card 120 is preferably formed of a paper-board material which is relatively durable, but yet capable of being folded in a manner to be hereinafter described. However, the card 120 could be formed of other materials which have foldable sections, as for example, plastic sheets which are hingedly connected through thin plastic membranes such that the various components of the card 120 can be folded with respect to each other, as illustrated in FIG. 9.

The card 120 is comprised of a first card plate 122 which serves as a lower card plate. The card plate 122 is generally rectangular in shape having rounded corner margins. Moreover, the card plate 122 has a transverse dimension approximately equal to or slightly less than the transverse dimensions of the opening 30 and the recessed area 32. However, the card plate 122 has a longitudinal dimension which is somewhat greater than the opening 30. The card plate 122 is connected to an intermediate card plate 124 which is also somewhat rectangular in shape, through a fold line 126. The card plate 124 generally has a longitudinal dimension approximately equal to the overall vertical thickness of the pad 10 or the depth thereof when flatwise on a supporting surface. Moreover, the card plate 124 has a width which is equal to or slightly less than the width or transverse dimension of the opening 30. The card plate 124 will serve as a vertically disposed card section in a manner to be herinafter described in more detail.

The card plate 124 is connected to another card plate 128 through another fold line 130. The card plate 128 is similarly rectangular in shape and is provided with rounded corner margins in the manner as illustrated in FIG. 9. Again, the transverse dimension or width of the card plate 128 is approximately equal to or slightly less than the width or transverse dimension of the opening 30. However, the longitudinal dimension of the card plate 128 is approximately equal to the longitudinal dimension of the opening 30 including the recessed area 32. The card plate 128 will serve as an upper card section in a manner also to be hereinafter described in more detail.

Finally, the card plate 128 is connected to a tab 132 through a fold line 134 on its right-hand transverse end portion. The tab 132 has a longitudinal dimension approximately equal to or less than the depth of the shelf 38, that is the dimension between the upper surface of the shelf 38 to the top wall 14. Moreover, the tab 132 has a width or transverse dimension equal to or slightly less than the transverse dimension of the opening 30 and the shelf 38. The tab 132 will also serve as a vertically disposed section when in use, in a manner also to be hereinafter described in more detail.

In order to package the components of the apparatus, the hose 68 and the nozzle 50 can be conveniently stored within the pad 10 in the manner as more fully illustrated in FIGS. 11 and 12 of the drawings. In order to store the components, the bottom wall 12 is placed upon a flat supporting surface, as for example a table or the like. The card plate 122 is disposed beneath the opening 30 and engages an underportion of the bottom wall 12 beneath the shelf 38. The card plate 124 is bent into an upright position so that it is vertically disposed and engages the interior transverse end wall 40. The nozzle 50 is then disposed in one of the elongate recesses 44 such that the shank 52 is accommodated in the recess 44 and the enlarged head 58 extends beyond the recess 44 so that the shoulder 76 engages the groove 46.

The hose 68 is next rolled up in a fairly tight rolled configuration in the manner as illustrated in FIG. 12. Thereafter, the hose is inserted within the opening 30 and can have a portion thereof partially disposed on the shelf 38 in the recessed area 36. The insert 80 is then turned upside-down so that the bottom surface is presented upwardly and is placed over the shelf 38. The insert 80 is positioned so that the vertical plate 94 and the peripheral side walls 80, 90 and 92 extend downwardly into the opening 30, with plate 94 located adjacent the transverse end margin 39 of the shelf 38. Thus, the insert 80 will retentively hold the nozzle 50 within the central recess 44.

It can be observed that the central recess 102 in the upper surface of the bottom wall 84 is sized to accommodate the shank 52 of the nozzle 50. Moreover, the upwardly extending projections 98 will fit within the corresponding outermost recesses 44 on the shelf 38. Thus, the lower surface of the insert 80 which is now upwardly disposed will be generally planar with or flush with the top wall 14. In the preferred aspect, the upwardly presented surface of the insert 80, when turned over, and at least the projections 106 and 108 may be located very slightly below the surface of the top wall 14.

After the nozzle 50 and the hose 68 have been disposed within the opening 30 and on the shelf 38 as previously described and partially retained by the insert 80, the card 120 is used to hold each of these components in their packaged position. The card plate 128 which serves as the top card plate is bent over into a position where it is essentially parallel to the card plate 122. The card plate 128 has a size such that it extends across the opening 30 and the recessed area 32 and fits snugly within this opening and recessed area. The tab 132 is bent downwardly so that it is disposed in a vertical direction and engages the interior transverse wall section 34. In this way, the card 120 completely encloses all of the previous components within the pad 10.

It is again quite easy to remove each of the components by merely lifting the tab 132 outwardly and lifting the card plate 128 upwardly. In this way, it is possible to remove the insert 80 along with the hose 68 and the nozzle 50. The device can then be connected as previously described for use. Again, upon dismantling, the various components can be easily packaged again with the pad 10.

The upwardly presented surface of the card plate 128 when in the packaged position can also be provided with instructions, manufacturing identification and like information. Moreover, the entire package can be included within a transparent plastic wrapper for purpose of marketing, as for example, shrink packaging and the like.

Thus, there has been illustrated and described a unique and novel apparatus and method for treating human ailments by means of directed liquid spray and which therefore fulfills all of the advantages and objects sought therefor. It should be understood that many changes, modifications, variations and other uses and applications will become apparent to those skilled in the art after considering this disclosure and the accompanying drawings. Therefore, any and all such changes, modifications, variations and other uses and applications which do not depart from the spirit and scope of the invention are deemed to be covered by the invention which is limited only by the following claims.

Having thus described my invention, what I desire to claim and secure by letters patent is:

1. A therapeutic spray device for treating groin and anal areas of human beings to relieve prostate or vaginal or anal ailments and conditions thereof, said device comprising:

(a) a pad having an upper supporting surface with a large opening therein and defining at least a pair of spaced apart front and rear elements therein said pad capable of supporting the buttocks of an individual in an approximate sitting position with relatively flat surfaces on said pad supporting portions of the thighs of such individual, or in position where the knees of the individual are supported on said relatively flat surfaces when in an approximate kneeling position, (b) said pad having a generally vertical nozzle receiving aperture in the front of said spaced apart elements and which is spaced forwardly of said opening, (c) a nozzle capable of being disposed in said aperture and capable of being connected to a source of liquid under pressure, said nozzle having at least one aperture located to be directed toward the groin and anal areas of a person sitting or kneeling on said pad, said nozzle being located relative to a person disposed on said pad so that it is not readily adaptable for insertion in a body cavity and is capable of emitting a spray of said liquid toward said anal or groin areas to treat or alleviate at least prostrate or vaginal or anal ailments and with the waste liquid passing through said opening, (d) connection means on said nozzle for connection to a source of liquid under pressure, (e) and said pad having a groove means angularly disposed to said nozzle receiving aperture and intersecting said nozzle receiving aperture to receive said connection means.

2. The spray device of claim 1 further characterized in that said spray device comprises a plurality of apertures in said pad and which also serve as engagement areas for grasping by the fingers of a human being for carrying and when said nozzle is sized to fit in each said aperture for selective placement in any one of said apertures.

3. The spray device of claim 1 further characterized in that said device also comprises a flexible hose having one end capable of being removably connected to said connection means and an other end capable of being connected to a source of said liquid under pressure.

4. The spray device of claim 3 further characterized in that said liquid is water and said source of water under pressure is a conventional water tap.

5. The therapeutic spray device of claim 1 further characterized in that said pad is provided with an outer substantially water impervious skin.

6. The therapeutic spray device of claim 5 further characterized in that said skin is integral with the material forming said pad.

* * * * *